United States Patent
Vachon

Patent Number: 5,861,023
Date of Patent: Jan. 19, 1999

[54] THROMBUS AND TISSUE INGROWTH INHIBITING OVERLAYS FOR DEFIBRILLATOR SHOCKING COIL ELECTRODES

[75] Inventor: David J. Vachon, Granada Hills, Calif.

[73] Assignee: Pacesetter, Inc., Sylmar, Calif.

[21] Appl. No.: 991,111

[22] Filed: Dec. 16, 1997

[51] Int. Cl.$^6$ .................................................. A61N 1/05
[52] U.S. Cl. ........................................................ 607/121
[58] Field of Search .................................. 607/121, 122

[56] References Cited

U.S. PATENT DOCUMENTS

| | | | |
|---|---|---|---|
| 4,198,991 | 4/1980 | Harris | 128/784 |
| 4,327,747 | 5/1982 | Gold | 128/784 |
| 4,573,480 | 3/1986 | Hirshberg | 128/784 |
| 4,883,070 | 11/1989 | Hanson | 128/785 |
| 4,945,922 | 8/1990 | Krieken | 128/785 |
| 5,090,422 | 2/1992 | Dahl, et al. | 128/784 |
| 5,238,007 | 8/1993 | Giele, et al. | 607/126 |
| 5,431,681 | 7/1995 | Helland | 607/4 |
| 5,466,252 | 11/1995 | Soukup, et al. | 607/116 |

FOREIGN PATENT DOCUMENTS

| | | |
|---|---|---|
| 2604165 | 8/1976 | Germany . |
| 9417852 | 8/1994 | WIPO . |

Primary Examiner—William E. Kamm

[57] ABSTRACT

An implantable lead includes a distal portion carrying a tissue-stimulating electrode having an outer surface and an inner surface, at least a portion of the outer surface of the electrode being adapted to stimulate cardiac tissue. At least one of the surfaces of the stimulating electrode includes an overlay of a sulfonated thermoplastic elastomer/rubber for minimizing adhesion and tissue ingrowth while passing sufficient electrical current to stimulate the tissue. The overlay may comprise a coating, film, tube, sleeve or other encapsulation. Sulfonated block copolymers of styrene-ethylene-butylene-styrene (SEBS), styrene-ethylene-propylene-styrene (SEPS), styrene-isoprene-styrene and styrene-isobutylene-styrene are effective to inhibit the formation of thrombus at the shocking electrode. In addition, when these copolymers absorb body fluids, they swell and infiltrate the interstices of the electrode coils thereby inhibiting tissue ingrowth. Furthermore, such materials, while non-porous, are conductive and thus do not impede the flow of electrical current at sulfonation levels above at least about 30%, with the optimal level residing between about 40% and about 70%. Although the above-described sulfonated block copolymers are preferred, other hydrogel-like materials may be employed including p-HEMA (polyhydroxymethacrylate), PEG (polyethylene glycol) acrylates, and cross-linked PVP (polyvinylpyrrolidone), and polyurethane hydrogels.

17 Claims, 2 Drawing Sheets

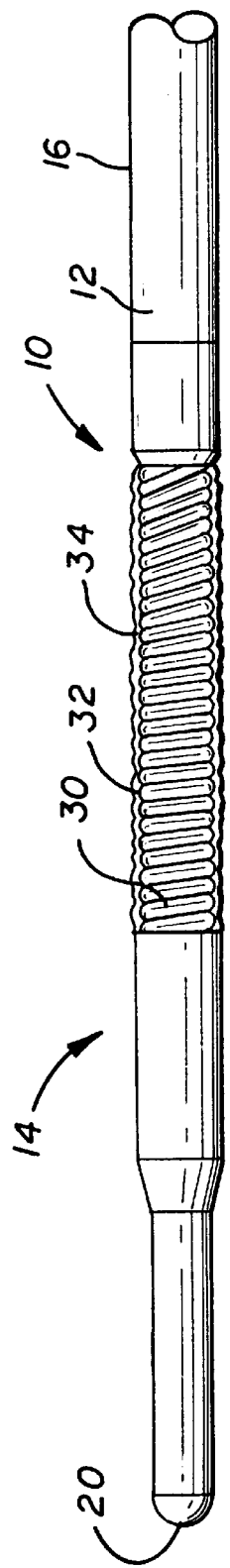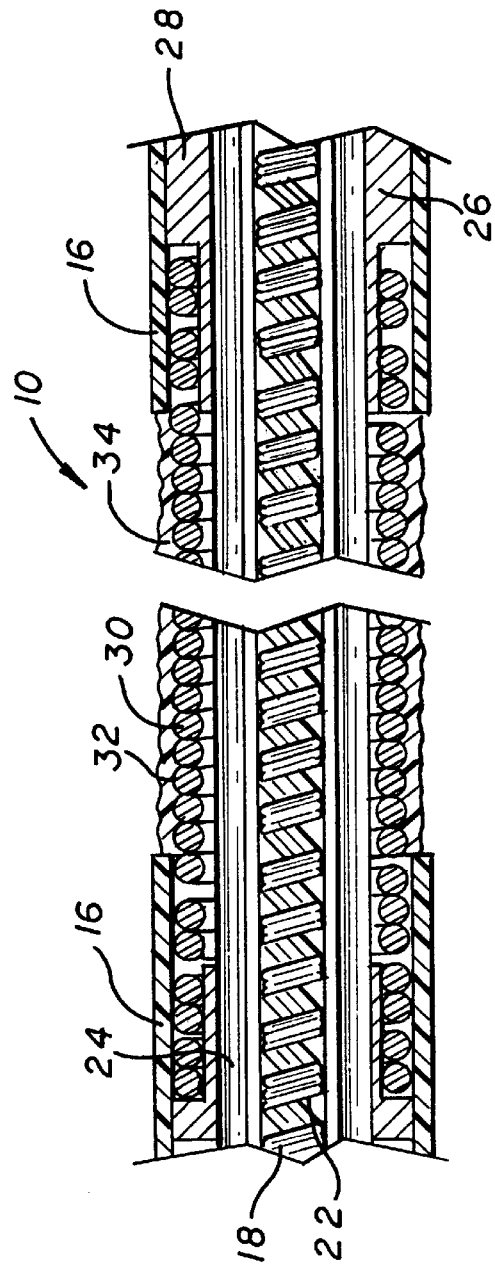

THROMBUS AND TISSUE INGROWTH INHIBITING OVERLAYS FOR DEFIBRILLATOR SHOCKING COIL ELECTRODES

FIELD OF THE INVENTION

The present invention relates generally to implantable leads and particularly to transvenous defibrillator leads having thrombus-inhibiting, biocompatible materials coating or otherwise covering the shocking electrodes of such leads.

BACKGROUND OF THE INVENTION

An automatic implantable cardioverter defibrillator (AICD) or implantable cardioverter defibrillator (ICD) detects ventricular fibrillation and delivers a series of countershocks of sufficient energy to terminate the fibrillation. Such an ICD utilizes an electrode system either attached to the outer surface of the heart by means of a large surface area patch electrode, or inserted transvenously into or near the heart. Such an ICD system may be combined with a pacemaker function.

Transvenous defibrillator leads for correcting ventricular tachycardia and ventricular fibrillation include uninsulated, helically wound shocking electrodes, formed of round wire, and rely on direct contact between the electrode and tissue or blood within or near the heart to deliver electrical energy to the heart.

The shocking coil of a chronically implanted, transvenous defibrillator lead poses two significant, yet different, problems. First, because the surface of a helical shocking coil is contoured and has a large area, it tends to encourage tissue ingrowth, that is, the growth of tissue into the interstices of the exposed coil windings. This tissue ingrowth can make removal of the lead difficult and in the event of post-op infection can present a significant risk to the patient in the event removal of the lead is required because of an uncorrectable device malfunction. Extensive surgical intervention may be required with a concomitant lengthy recovery time. Secondly, transvenous defibrillator leads with shocking electrodes formed from round wire and inserted within the superior vena cavae have a tendency to encourage the attachment of red blood cells and platelets (thrombus). More specifically, the high energy densities can produce instantaneous temperatures high enough to denature surface proteins, damage platelets and alter cell membrane potentials to such an extent as to initiate thrombosis. A lack of hemocompatibility as described can result in emboli which pose serious risks, the accumulation of thrombus at the shocking electrode being potentially damaging to the patient since these can lead to a decrease in blood flow, infarct or stroke.

It is known to coat or otherwise cover a helically wound transvenous defibrillator electrode with an electrically conductive polymeric material for inhibiting tissue ingrowth, thus reducing the risk to the patient in the event removal of the lead becomes necessary. One such material is PTFE, a porous, biocompatible insulating material that becomes conductive as body fluids penetrate the pores. The small pore sizes, however, tend to inhibit tissue ingrowth.

U.S. Pat. No. 5,090,422 discloses an ICD lead including an endocardial helically wound electrode covered with a thin coating membrane of biocompatible porous material relatively inert to bodily fluids. The material is preferably constructed of a polyurethane foam or other biocompatible, relatively soft polymeric material that can be produced within the desired range of pore sizes. Particular materials that are disclosed in the '422 patent include woven, porous polyurethane and porous polytetrafluoroethylene (PTFE) used with a wetting agent or with a modified surface. The '422 patent proposes materials having an average surface pore size less than about 15 to 20 microns to ensure a dissection plane which precludes significant tissue ingrowth yet allows the penetration or passage of bodily fluids thereby reducing the electrical resistance and minimizing ohmic losses in the system.

U.S. Pat. No. 4,573,480 relates to an implantable cardiac pacemaker lead covered with an insulating sheath made of porous PTFE instead of the more commonly used silicone rubber or polyurethane. The sizes of the pores are selected to combine high flexibility with sufficient imperviousness to body fluid. The insulation can have areas of varying porosity along its length. For example, in the vicinity of the electrodes, areas with large pores serve to ensure that this part of the electrode will grow in after the implantation.

SUMMARY OF THE INVENTION

In accordance with one specific form of the present invention, there is provided an implantable lead having a distal portion including a tissue-stimulating electrode having an outer surface and an inner surface, at least a portion of the outer surface of the electrode being adapted to stimulate cardiac tissue. At least one of the surfaces of the stimulating electrode includes an overlay of a sulfonated thermoplastic elastomer/rubber for minimizing adhesion and tissue ingrowth while passing sufficient electrical current to stimulate the tissue. The overlay may comprise a coating, film, tube, sleeve or other encapsulation.

It has been found that sulfonated block copolymers of styrene-ethylene-butylene-styrene (SEBS), styrene-butadiene, styrene-isoprene-styrene and styrene-isobutylene-styrene are effective to inhibit the formation of thrombus at the shocking electrode. In addition, when these copolymers absorb body fluids, they swell and infiltrate the interstices of the electrode coils thereby inhibiting tissue ingrowth. Furthermore, such materials, while nonporous, are conductive and thus do not impede the flow of electrical current at sulfonation levels above at least about 30%, with the optimal level residing between about 40% and about 70%. In contrast with PTFE, such materials do not need to be treated with wetting agents or require surface modification. Further, these materials are particularly advantageous when used to overlay the outer surface of the stimulating electrode because of their superior structural integrity when fully hydrated.

Moreover, a tube or tube-like structure fabricated of such materials can be inserted inside the shocking coil electrode in contact with the inner surface thereof. Absorption of body fluids causes the material to swell and to occupy the spaces between adjacent coil windings. Not only does the swollen material thereby inhibit thrombosis and tissue ingrowth, but infiltration of body fluids into the interior of the lead is also prevented. Instead of an inner tube constructed of the described copolymers, a tubular substrate impregnated with such copolymers or a coating on the surface of the internal insulation sheath or a coating on the inner surface of the shocking electrode can be used.

Although the above-described sulfonated block copolymers are preferred in the practice of the present invention, other hydrogel-like materials may be employed including p-HEMA (polyhydroxymethacrylate), PEG (polyethylene glycol) acrylates, and cross-linked PVP (polyvinylpyrrolidone), and PVA (polyvinyl alcohol), and polyacrylamide and polyurethane hydrogels.

BRIEF DESCRIPTION OF THE DRAWINGS

Further objects, features and advantages of the invention will become apparent from the Detailed Description of the Preferred Embodiments, below, when read in conjunction with the accompanying drawings, in which:

FIG. 1 is a side view of a portion of a pacing and defibrillation lead according to the present invention;

FIG. 2 is an axial cross section view of a portion of the lead of FIG. 1 showing a helical shocking coil electrode with an external overlay comprising a coating, tube or sleeve in accordance with one embodiment of the invention;

DETAILED DESCRIPTION OF THE PREFERRED EMBODIMENTS

Figure 3:
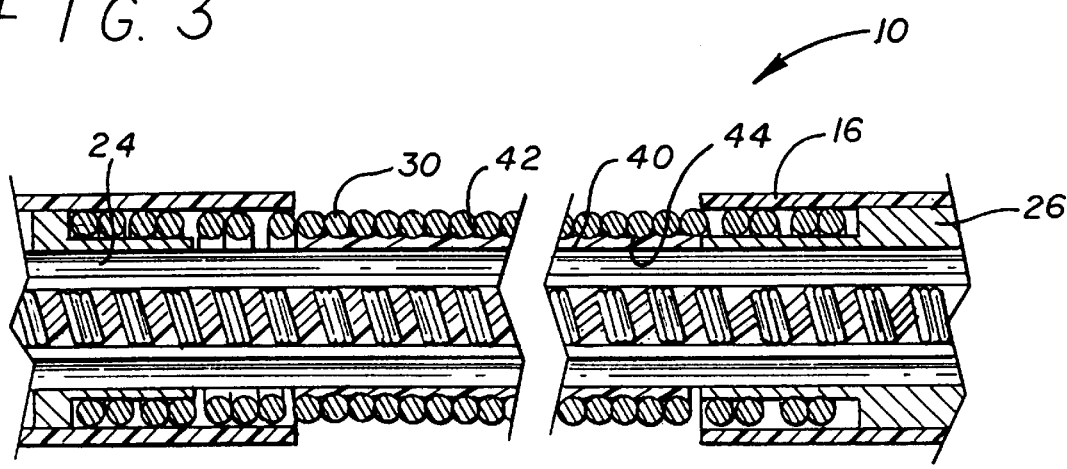
FIG. 3 is an axial cross section view of a portion of a lead showing a helical shocking coil electrode disposed about an internal, gel impregnated tubular substrate in accordance with an alternative embodiment of the invention.

The following description presents a preferred embodiment of the invention representing the best mode contemplated for practicing the invention. This description is not to be taken in a limiting sense but is made merely for the purpose of describing the general principles of the invention whose scope is defined by the appended claims.

FIGS. 1 and 2 of the drawings depict portions of a transvenous combined pacing and defibrillation lead 10 designed for intravenous insertion and contact with either tissue or blood. The lead 10 comprises an elongated lead body 12 interconnecting a proximal end (not shown) and a distal end 14. The lead 10 further includes coiled or helically wound electrical conductors covered with an insulating sheath 16. The insulating sheath 16 is preferably fabricated of silicone rubber, polyurethane or other suitable biocompatible, biostable elastomer. As is well known in the art, the proximal end of the lead 10 has a connector assembly provided with sealing rings and typically carrying a plurality of electrical contacts connected to the helically wound electrical conductors of the lead.

More specifically, the lead 10 includes an inner, multifilar helical coil conductor 18 extending through the lead body 12 from the connector at the proximal end to a tip electrode 20 on the distal end 14 of the lead 10. The helical coil conductor 18 defines the walls of a hollow interior 22 of the lead 10 which interior accepts a stylet during lead implantation. Disposed about and coaxially of the inner coil conductor 18 is an insulating sleeve 24. The lead body 12 further includes a tubular, electrically conductive connector 26 having a proximal end 28 connected, by means of a helical coil conductor, to the connector assembly at the proximal end of the lead. This structure may be of the kind disclosed in U.S. Pat. No. 5,431,681 which is incorporated herein by reference. Electrically connected to the tubular connector 26 is a helically wound shocking coil 30 having an outer surface 32 and fabricated of wire typically having a round cross section. The structural details of such shocking coils are well known in the art; suffice it to say that, as disclosed, for example, in the incorporated U.S. Pat. No. 5,431,681, the coils normally present an outer, bare surface to tissue or blood and that the coil windings have a pitch that may vary depending upon the lead design, also as well known in the art. The shocking coil 30 shown in the embodiment of FIGS. 1 and 2 has a close pitch, adjacent coil windings being in contact with each other, or nearly so, for ease of manufacture and reduced cost.

As explained, because shocking coils present a large, convoluted surface area to tissue or blood, tissue ingrowth can be promoted between adjacent shocking coil windings making subsequent removal of the lead difficult. In addition, the high energy density applied by the shocking coil can initiate thrombosis and the formation of emboli presenting serious risks to the patient.

To address these problems, the outer surface 32 of the shocking coil 30 is provided with an encapsulating coating or tubular sleeve 34 preferably comprising a biocompatible, biostable, non-water soluble hydrogel-like material. It has been found that sulfonated block copolymers of styrene-ethylenebutylene-styrene (SEBS), styrene-butadiene, styrene-isoprene-styrene and styrene-isobutylene-styrene are effective to inhibit the formation of thrombus at the shocking electrode. Furthermore, while nonporous, these materials do not impede the flow of electrical current at sulfonation levels above at least about 30%, with the optimal level residing between about 40% and about 70%. These hydrogel-like materials can be processed into lacquers allowing them to be readily applied as coatings. When these coatings have absorbed water (that is, hydrated to 50–200%), they remain tough unlike conventional hydrogels which have a tendency to rip, peel and tear.

Alternatively, hydrogel-like materials such as p-HEMA (polyhydroxymethacrylate), PEG (polyethylene glycol) acrylates, and cross-linked PVP (polyvinylpyrrolidone), and PVA (polyvinyl alcohol), and polyacrylamide and polyurethane hydrogels may be used for the overlay 34.

Figure 4:
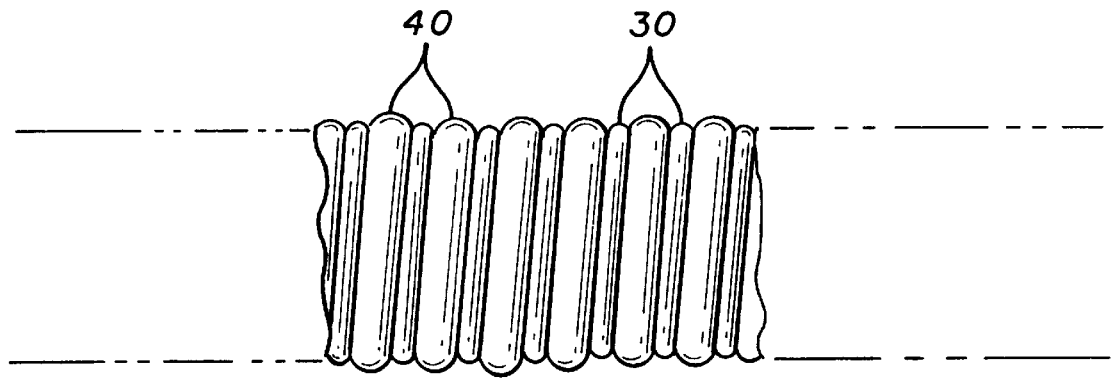
FIG. 4 is a side view of a helical shocking coil electrode along the lines of that of FIG. 3 showing its configuration (in exaggerated form) after the gel impregnated tubular substrate has swollen.

Turning now to FIGS. 3 and 4, there is shown an alternative embodiment of the invention in which, instead of enveloping the outer surface of the shocking coil with an overlay of hydrogel-like material, an overlay 40, fabricated from any of the above-described hydrogel-like materials, is disposed inside the shocking coil 30. As before, the overlay 40 may take the form of a coating, a tube or other encapsulation. Where the overlay 40 takes the form of a tube, such tube may be formed of a film or sheet strip folded or rolled into a tube-like structure with the edges of the strip in abutting or near abutting relationship, or overlapping. Where the overlay 40 is in the form of a coating, such coating can be applied to the inner surface 44 of the electrode by means of a dipping operation with the outer surface of the electrode masked. Alternatively, the coating 40 may be applied to the outer surface of the insulating sleeve 24. In any case, the overlay 40 has an outer surface 42 in contact with the inner surface 44 of the coil 30. When the distal end 14 of the lead 10 is placed in contact with physiologic fluids (blood), the hydrogel-like material absorbs fluid and swells thereby occupying the interstices between adjacent windings of the coil 30 (FIG. 4). Not only does the presence of the hydrogel deter thrombus at the shocking coil electrode but the swollen hydrogel prevents infiltration of body fluids into the interior space between the shocking coil and the tip electrode conductors.

As an alternative to an overlay 40 in the form of a tube or tube-like structure, a tubular substrate such as woven polyethylene terephthalate (PET/Dacron), impregnated with any of the described hydrogel materials, may be used.

To test the embodiment of FIGS. 3 and 4, a 0.060 inch diameter gauge pin was dip coated five (5) times with a solution of SEBS-SO₃H hydrogel that was 37% sulfonated. The pin was inserted into the interior of a superior vena cava shocking coil electrode and the combination added to room temperature water. After about 30 minutes, the swollen gel was clearly visible in the coil interstices. A somewhat exaggerated depiction of what was observed is shown in FIG. 4

The described materials can be compounded with various therapeutic agents (steroids, proteins, anticoagulents and the like). Steroids, for example, may help minimize any inflammation during the healing response.

In summary, the shocking electrode of an ICD lead is perhaps the most critical component of the lead for several reasons. One critical feature of such coil electrodes is that they have the potential for encouraging the adhesion of cells resulting in the growth and ingrowth of tissue into and around the electrode. Such a phenomenon renders the lead nearly impossible to remove should the patient's condition necessitate such a procedure. Another problem is the potential formation of thrombus and emboli at the shocking electrode. The present invention provides a straightforward and simple solution to these problems without effecting the electrical performance of the electrode.

It should be appreciated that the foregoing description is only illustrative of the invention. Various alternatives and modifications can be devised by those skilled in the art without departing from the spirit of the invention. For example, it will be evident that an overlay of the materials in accordance with the present invention may be applied to the outer surface of a lead body along the entire length of the lead body. Further, besides their utility as coverings for shocking electrodes, it will be evident that materials in accordance with the present invention may be used to coat heart valves, patch electrodes and other chronically implanted devices. Accordingly, the present invention is intended to embrace all such alternatives, modifications and variations as fall within the scope of the appended claims.

What is claimed is:

1. An implantable lead having a distal portion including a stimulating electrode having an outer surface at least a portion of which is adapted to stimulate cardiac tissue, and an inner surface, at least one of the surfaces of the stimulating electrode including an overlay of a sulfonated thermoplastic elastomer/rubber for minimizing adhesion and tissue ingrowth while passing sufficient electrical current to stimulate the tissue.

2. An implantable lead, as defined in claim 1, in which the sulfonated thermoplastic elastomer/rubber has a sulfonation level of at least about 30%.

3. An implantable lead, as defined in claim 2, in which the sulfonated thermoplastic elastomer/rubber has a sulfonation level between about 40% and about 70%.

4. An implantable lead, as defined in claim 1, in which the sulfonated thermoplastic elastomer/rubber comprises styrene-ethylene-butylene-styrene.

5. An implantable lead, as defined in claim 1, in which the sulfonated thermoplastic elastomer/rubber comprises styrene-butadiene.

6. An implantable lead, as defined in claim 1, in which the sulfonated thermoplastic elastomer/rubber comprises styrene-isoprene-styrene.

7. An implantable lead, as defined in claim 1, in which the sulfonated thermoplastic elastomer/rubber comprises styrene-isobutylene-styrene.

8. An implantable lead having a distal portion including a stimulating electrode having an outer surface at least a portion of which adapted to stimulate cardiac tissue, and an inner surface, at least one of said surfaces including an overlay of a hydrogel-like, sulfonated thermoplastic elastomer/rubber selected from the group consisting of styrene-ethylene-butylene-styrene, styrene-butadiene, styrene-isoprene-styrene and styrene-isobutylene-styrene, for minimizing adhesion and tissue ingrowth while passing sufficient electrical current to stimulate the tissue.

9. An implantable lead, as defined in claim 8, in which the stimulating electrode is a defibrillation shocking coil electrode.

10. An implantable lead, as defined in claim 9, in which the hydrogel-like material is in the form of a coating or sleeve encapsulating the outer surface of the electrode.

11. An implantable lead, as defined in claim 9, in which the hydrogel-like material is in the form of a tube disposed in contact with the inner surface of the electrode.

12. An implantable lead, as defined in claim 9, in which the hydrogel-like material is impregnated in a tubular substrate disposed in contact with the inner surface of the electrode.

13. An implantable lead having a distal portion including a stimulating electrode having an outer surface at least a portion of which adapted to stimulate cardiac tissue, and an inner surface, at least one of said surfaces including an overlay of a hydrogel-like material selected from the group consisting of p-HEMA (polyhydroxymethacrylate), PEG (polyethylene glycol) acrylates, and cross-linked PVP (polyvinylpyrrolidone), and PVA (polyvinyl alcohol), and polyacrylamide and polyurethane hydrogels for minimizing adhesion and tissue ingrowth while providing sufficient electrical current to stimulate the tissue.

14. An implantable lead, as defined in claim 13, in which the stimulating electrode is a defibrillation shocking coil electrode.

15. An implantable lead, as defined in claim 14, in which the hydrogel-like material is in the form of a coating or sleeve encapsulating the outer surface of the electrode.

16. An implantable lead, as defined in claim 14, in which the hydrogel-like material is in the form of a tube disposed in contact with the inner surface of the electrode.

17. An implantable lead, as defined in claim 14, in which the hydrogel-like material is impregnated in a tubular substrate disposed in contact with the inner surface of the electrode.

* * * * *